(12) United States Patent
Isogai et al.

(10) Patent No.: US 7,971,482 B2
(45) Date of Patent: Jul. 5, 2011

(54) HUMIDITY SENSOR

(75) Inventors: Toshiki Isogai, Nagoya (JP); Toshikazu Itakura, Toyota (JP)

(73) Assignees: Denso Corporation, Kariya (JP); Nippon Soken, Inc., Nishio (JP)

( * ) Notice: Subject to any disclaimer, the term of this patent is extended or adjusted under 35 U.S.C. 154(b) by 177 days.

(21) Appl. No.: 12/081,513

(22) Filed: Apr. 17, 2008

(65) Prior Publication Data

US 2008/0257037 A1 Oct. 23, 2008

(30) Foreign Application Priority Data

Apr. 20, 2007 (JP) ................................. 2007-112136

(51) Int. Cl.
*G01N 27/22* (2006.01)
(52) U.S. Cl. .................................... 73/335.04; 324/664
(58) Field of Classification Search .................. 324/663, 324/664, 665, 666, 669, 670; 73/335.02, 73/335.03, 335.04
See application file for complete search history.

(56) References Cited

U.S. PATENT DOCUMENTS

| 5,656,928 | A | 8/1997 | Suzuki et al. | |
| 6,580,600 | B2 | 6/2003 | Toyoda et al. | |
| 2002/0114125 | A1 | 8/2002 | Toyoda et al. | |
| 2004/0182153 | A1* | 9/2004 | Hamamoto | 73/335.04 |
| 2006/0096370 | A1* | 5/2006 | Isogai et al. | 73/335.04 |

FOREIGN PATENT DOCUMENTS

| JP | U-S59-179366 | 11/1984 |
| JP | A-01-292244 | 11/1989 |
| JP | A-2002-052337 | 2/2002 |
| JP | A-2003-130833 | 5/2003 |

OTHER PUBLICATIONS

Karube, S. "Water Retention, Adsorption, and Microstructure of Allophane and Imogolite." 45$^{th}$ Symposium of Soil Phu=ysics Society, Nov. 22, 2003, at Univ. Okayama.*
E.C. Dickey, O. K. Varghese, K. G. Ong, M. Paulose, and C. A. Grimes, "Room Temperature Ammonia and Humidity Sensing Using Highly Ordered Nanoporous Alumina Films." Sensors 2 (2002) pp. 91-110.*
Hygrometrix, Inc., Applications Note 2004-2. "A comparison of relative humidity sensing technologies." pp. 1-5, (2004).*
Office Action mailed Jul. 7, 2009 from the Japan Patent Office in the corresponding JP application No. 2007-112136 (and English Translation).

* cited by examiner

*Primary Examiner* — Lisa M Caputo
*Assistant Examiner* — Punam Roy
(74) *Attorney, Agent, or Firm* — Posz Law Group, PLC (57) ABSTRACT

A capacitive humidity sensor includes: a humidity sensing element with a humidity sensitive film and electrodes; and a processing circuit. The film has a dielectric constant variable in accordance with moisture. The electrodes detect capacitance of the film and outputs a signal corresponding to the capacitance. The processing circuit processes the signal. The film is made of inorganic material having fine pores for adsorbing the moisture. A diameter of the fine pores is set to be a predetermined diameter so that capillary tube aggregation phenomenon occurs at a predetermined relative humidity. The capacitance of the film has a change rate with respect to the relative humidity. The change rate in case of the relative humidity higher than the predetermined relative humidity is larger than that in case of the relative humidity lower than the predetermined relative humidity.

9 Claims, 9 Drawing Sheets

RELATED ART

HUMIDITY SENSOR

CROSS REFERENCE TO RELATED APPLICATION

This application is based on Japanese Patent Application No. 2007-112136 filed on Apr. 20, 2007, the disclosure of which is incorporated herein by reference.

FIELD OF THE INVENTION

The present invention relates to a humidity sensor.

BACKGROUND OF THE INVENTION

A humidity sensor for detecting humidity of atmosphere around the sensor is disclosed in, for example, JP-A-2002-243690 corresponding to U.S. Pat. No. 6,580,600. The sensor includes a semiconductor substrate, a silicon oxide film on the substrate, a pair of electrodes disposed on the same plane of the silicon oxide film so as to separate from each other, a silicon nitride film covering the electrodes, and a humidity sensitive film disposed on the silicon nitride film. The humidity sensitive film covers the electrodes and is disposed between the electrodes. A capacitance between the electrodes is changeable in accordance with humidity of atmosphere around the sensor. Based on the capacitance, the humidity is detected by the sensor.

Figure 14:
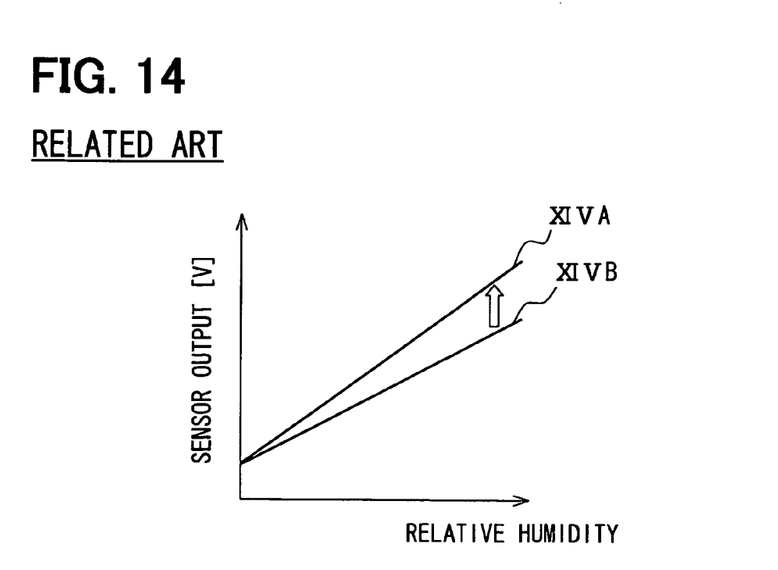
FIG. 14 is a graph showing a relationship between relative humidity and a sensor output in different humidity sensors.

The humidity sensitive film is made of hygroscopic organic polymer such as poly-imide and butyric acetylcellulose. The organic polymer providing the humidity sensitive film includes numerous molecules, each of which has a long chain shape, and the numerous molecules densely intertwine with each other. When the sensor is left for a long time in high humid atmosphere, the molecular group of the organic polymer untwines gradually due to water molecules in the atmosphere. The untwined polymer can adsorb water molecules more than the intertwined polymer under the same condition. Thus, the humidity sensitive film composed of the untwined polymer can adsorb water molecules in the atmosphere more than the humidity sensitive film composed of the intertwined polymer under the same humidity condition. This phenomenon is defined as swelling phenomenon. When the humidity sensitive film adsorbs much water molecules, as shown in FIG. 14, a sensor output increases even when relative humidity is the same. Here, a curve XIVA represents a relationship between a sensor output of a humidity sensor and relative humidity when the sensor is used for a long time so that the humidity sensitive film adsorbs much water molecules. A curve XIVB represents a relationship between a sensor output of a humidity sensor and relative humidity when the sensor is not substantially used after the sensor is manufactured. Thus, the sensor output in the humidity sensor is deviated, so that detection accuracy of the relative humidity in the atmosphere is reduced. Thus, it is required for the humidity sensor to maintain the detection accuracy for a long time.

SUMMARY OF THE INVENTION

In view of the above-described problem, it is an object of the present disclosure to provide a humidity sensor.

According to a first aspect of the present disclosure, a humidity sensor for detecting humidity in atmosphere includes: a humidity sensing element including a humidity sensitive film and a pair of first electrodes; and a processing circuit. The humidity sensitive film has a dielectric constant, which is variable in accordance with moisture adsorbed in the humidity sensitive film. The pair of first electrodes detects capacitance of the humidity sensitive film and outputs a signal corresponding to the capacitance. The processing circuit processes the signal from the pair of first electrodes. The humidity sensor is a capacitive humidity sensor for detecting relative humidity based on the dielectric constant of the humidity sensitive film. The humidity sensitive film is made of inorganic material having a plurality of fine pores for adsorbing the moisture in the atmosphere. A diameter of the fine pores is set to be a predetermined diameter so that capillary tube aggregation phenomenon occurs at a predetermined relative humidity. The capillary tube aggregation phenomenon is defined in such a manner that a plurality of water molecules in the atmosphere rapidly penetrate into the fine pores at the predetermined relative humidity. The capacitance of the humidity sensitive film has a change rate with respect to the relative humidity. The change rate of the capacitance when the relative humidity in the atmosphere is higher than the predetermined relative humidity is larger than the change rate of the capacitance when the relative humidity in the atmosphere is lower than the predetermined relative humidity.

In the above sensor, even when the sensor is used for a long time, initial detection accuracy is maintained since the inorganic material has stable physical property.

According to a second aspect of the present disclosure, a humidity sensor for detecting humidity in atmosphere includes: a humidity-sensing element including a humidity sensitive part, a detection part and a support part; and a processing circuit. The humidity sensitive part is made of inorganic material having a plurality of fine pores for adsorbing the moisture in the atmosphere. The support part supports the humidity sensitive part in such a manner that the humidity sensitive part is capable of vibrating. The humidity sensitive part vibrates with a resonant frequency corresponding to weight of moisture adsorbed in the humidity sensitive part. The resonant frequency of the humidity sensitive part is variable in accordance with the moisture adsorbed in the humidity sensitive part. The detection part detects vibration of the humidity sensitive part and outputs a signal corresponding to an amplitude of vibration of the humidity sensitive part. The processing circuit processes the signal from the detection part. The humidity sensor is a vibration type humidity sensor for detecting relative humidity based on the resonant frequency of the humidity sensitive part.

In the above sensor, even when the sensor is used for a long time, initial detection accuracy is maintained since the inorganic material has stable physical property.

According to a third aspect of the present disclosure, a humidity sensor for detecting humidity in atmosphere includes: a first element including a humidity sensitive film and a pair of first comb-teeth electrodes; a second element including a pair of second comb-teeth electrodes; and a processing circuit including a switched capacitor circuit, a switching circuit and first and second amplifiers. The humidity sensitive film has a dielectric constant, which is variable in accordance with moisture adsorbed in the humidity sensitive film. The pair of first comb-teeth electrodes is covered with the humidity sensitive film so that the pair of first comb-teeth electrodes detects capacitance of the humidity sensitive film. The pair of first comb-teeth electrodes outputs a signal corresponding to the capacitance. The humidity sensitive film is made of inorganic material having a plurality of fine pores for adsorbing the moisture in the atmosphere. A diameter of the fine pores has a predetermined distribution around a predetermined diameter. The diameter of the fine pores is disposed in a range between 10 nanometers and 50 nanometers. The predetermined distribution is disposed in a range between the predetermined diameter minus 1 nanometer and the predetermined diameter plus 1 nanometer. The second element has a capacitance, which is substantially constant with respect to the moisture in the atmosphere. The switched capacitor circuit converts a capacitance difference between the pair of second comb-teeth electrodes and the pair of first comb-teeth electrodes to a voltage. The first amplifier amplifies the voltage output from the switched capacitor circuit with a first amplification factor so that relative humidity higher than a predetermined relative humidity is detected. The second amplifier amplifies the voltage output from the switched capacitor circuit with a second amplification factor so that the relative humidity lower than the predetermined relative humidity is detected. The switching circuit switches between the first and second amplifiers based on the voltage output from the switched capacitor circuit.

In the above sensor, even when the sensor is used for a long time, initial detection accuracy is maintained since the inorganic material has stable physical property.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS

First Embodiment

FIGS. 1-7 show a humidity sensor 1 according to a first embodiment. The humidity sensor is, for example, a capacitive humidity sensor for detecting humidity based on dielectric constant of a humidity sensitive film.

Figure 1:
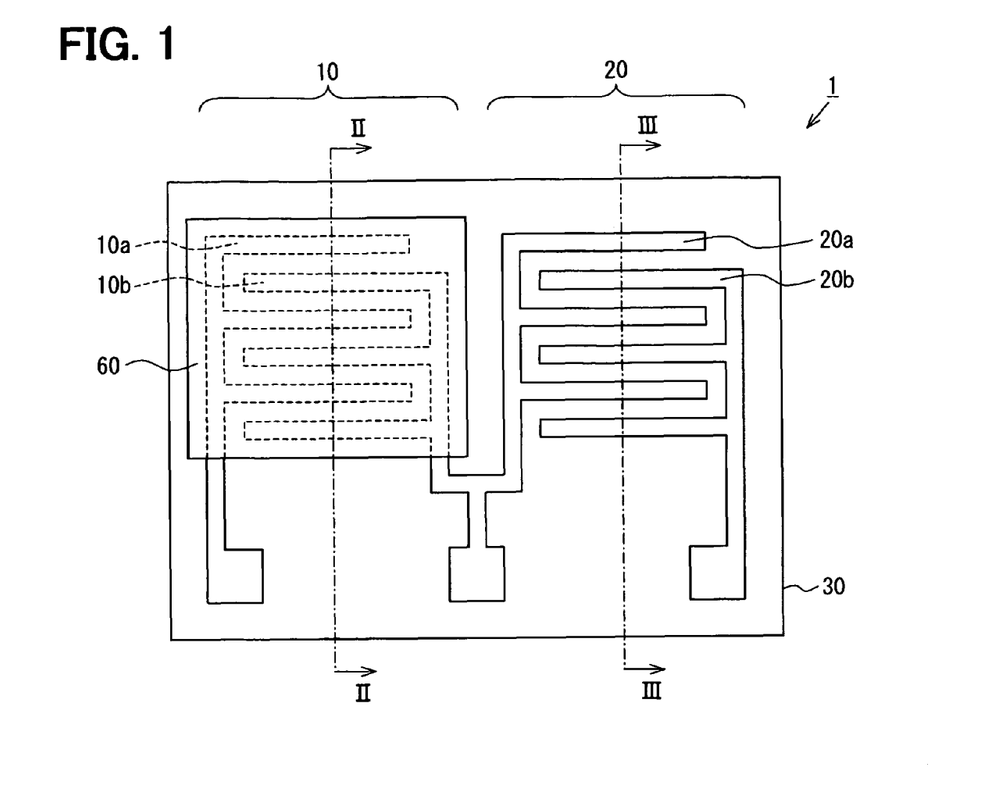
FIG. 1 is a plan view showing a humidity sensor according to a first embodiment.

The capacitive humidity sensor 1 includes a first sensor element 10 as a humidity sensor element and a second sensor element 20 as a second capacitive element.

Figure 2:
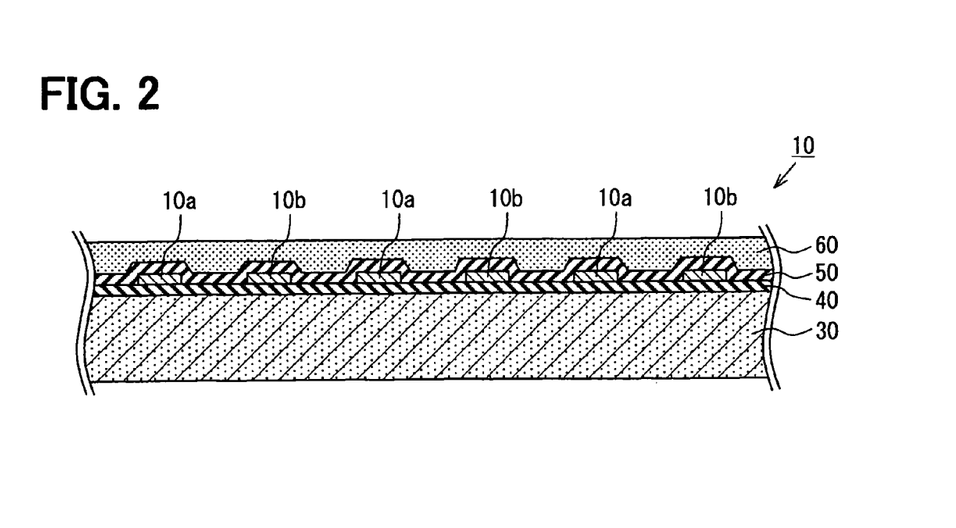
FIG. 2 is a cross sectional view showing the sensor taken along line II-II in FIG. 1.
Figure 3:
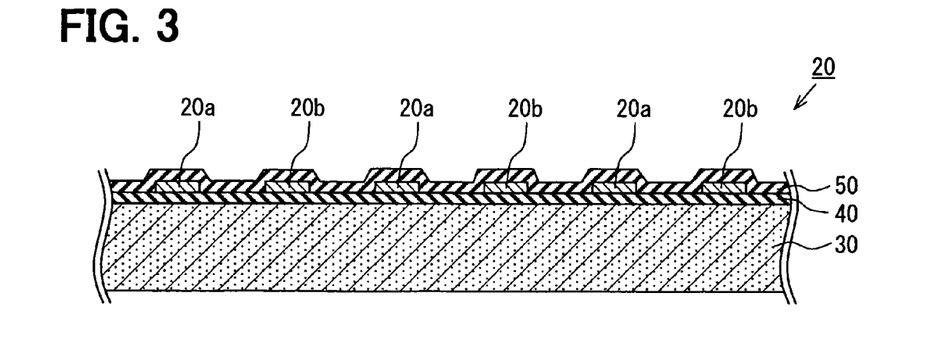
FIG. 3 is a cross sectional view showing the sensor taken along line III-III in FIG. 1.

As shown in FIGS. 2 and 3, the first and second sensor elements 10, 20 are formed on, for example, the same semiconductor substrate 30 made of silicon. An insulation film 40 made of silicon oxide is formed on the surface of the substrate 30. Two pairs of electrodes 10a, 10b, 20a, 20b for detecting relative humidity in atmosphere around the sensor 1 are formed on the insulation film 40, respectively. The electrodes 10a, 10b, 20a, 20b are made of metal such as aluminum, and separated from each other by a predetermined distance. The electrodes 10a, 10b, 20a, 20b are disposed on the same plane. The electrodes 10a, 10b, 20a, 20b may be made of Al—Si alloy, Ti, Au, Cu, poly-crystal silicon or the like. Here, the Al—Si alloy is mainly made of aluminum, and includes small amount of silicon. Although the electrodes 10a, 10b, 20a, 20b have a comb-teeth shape, the electrodes 10a, 10b, 20a, 20b may have another shape. The electrodes 10a, 10b, 20a, 20b are interleaved with each other. Specifically, comb-teeth of one electrode are interleaved with comb-teeth of the other electrode so that the comb-teeth of the one electrode face the comb-teeth of the other electrode. Accordingly, arrangement area of the total electrodes 10a, 10b, 20a, 20b are small. However, facing area of the electrodes 10a, 10b, 20a, 20b are large. Thus, the detection accuracy of the relative humidity in the sensor 1 is improved.

A protection film 50 protects the electrodes 10a, 10b, 20a, 20b from corrosion by moisture in atmosphere or water adsorbed on a humidity sensitive film 60. The protection film 50 made of SiN is formed on the electrodes 10a, 10b, 20a, 20b. The protection film 50 covers the electrodes 10a, 10b, 20a, 20b and disposed between the electrodes 10a, 10b, 20a, 20b. Here, when the protection film 50 covers at least the electrodes 10a, 10b, 20a, 20b, the electrodes 10a, 10b, 20a, 20b can be protected from the corrosion.

The humidity sensitive film 60 having multiple fine pores is formed on a part of the protection film 50 on the first sensor element side. The fine pores adsorb moisture in atmosphere. The humidity sensitive film 60 is made of inorganic material. Similar to the protection film 50, the humidity sensitive film 60 is formed to cover the electrodes 10a, 10b and to be disposed between the electrodes 10a, 10b. The humidity sensitive film 60 is formed on the substrate 30 by a dipping method or the like. Alternatively, the humidity sensitive film 60 may be formed by other methods.

When the moisture in the atmosphere is taken in the inside of the fine pores of the humidity sensitive film 60, although the dielectric constant of the humidity sensitive film 60 is not changed, the total dielectric constant of the humidity sensitive film 60 including the moisture adsorbed in the film 60 is changed in accordance with adsorbed moisture. This is because the moisture has large dielectric constant. Thus, the capacitance between the electrodes 10a, 10b is changed. The humidity change in the atmosphere is detected by the capacitance change between the electrodes 10a, 10b. The characteristics of the humidity sensitive film 60 will be explained as follows. No humidity sensitive film is formed on a part of the protection film 50 on the second sensor element side. Thus, the capacitance between the electrodes 20a, 20b is not changed in accordance with the humidity change in the atmosphere.

A signal processing circuit for processing an output signal from the first and second sensor elements 10, 20 is disposed on the surface portion of the substrate 30. The processing circuit includes a switched capacitor circuit as a C-V converter circuit, an amplifier, a switching circuit and the like.

The switched capacitor circuit converts the capacitance difference between the first and second sensor elements 10, 20 to a voltage. Specifically, the first sensor element 10 has a first capacitance between the electrodes 10a, 10b, and the second sensor element 20 has a second capacitance between the electrodes 20a, 20b. The capacitance difference between the first and second capacitances is converted to the voltage as a C-V converting value. The output voltage from the switched capacitor circuit is amplified with a predetermined amplification factor by the amplifier. The switching circuit switches the amplification factor of the amplifier. The processing circuit will be explained later.

An organic polymer such as polyimide for providing the humidity sensitive film in the sensor has a long chain shape, and numerous molecules of the polymer densely intertwine with each other. When the humidity sensor having the humidity sensitive film made of the organic polymer is left for a long time in high humid atmosphere such as at 65° C. and relative humidity of 90%, much moisture in the atmosphere is taken in the film even under the same humidity condition. Thus, swelling phenomenon occurs. When the swelling phenomenon occurs, the sensor output increases even when relative humidity is the same. Thus, the sensor output in the humidity sensor is deviated, so that detection accuracy of the relative humidity in the atmosphere is reduced.

However, inorganic material does not show the swelling phenomenon, in general. Specifically, the inorganic material has stable physical property, compared with the organic material, so that the physical property of the inorganic material does not change for a long time. Thus, in this embodiment, the humidity sensitive film 60 is made of the inorganic material, thereby, the initial detection accuracy of the sensor 1 with respect to the relative humidity in the atmosphere is maintained for a long time even when the sensor 1 is left for a long time.

Under the atmosphere having relative humidity lower than a predetermined relative humidity, small amount of moisture, i.e., small number of water molecules penetrates in the inside of the fine pores of the humidity sensitive film 60. However, under the atmosphere having relative humidity higher than the predetermined relative humidity, the amount of moisture, i.e., the number of water molecules to penetrating in the inside of the fine pores rapidly increases. This is a capillary tube aggregation phenomenon. Here, when the water molecules penetrate in the fine pores, the total dielectric constant of the sensor 1 rapidly increases, and further, the capacitance rapidly increases. The present inventors confirm that the predetermined relative humidity as a threshold of the capillary tube aggregation phenomenon strongly relates to a diameter of the fine pore.

Figure 4:
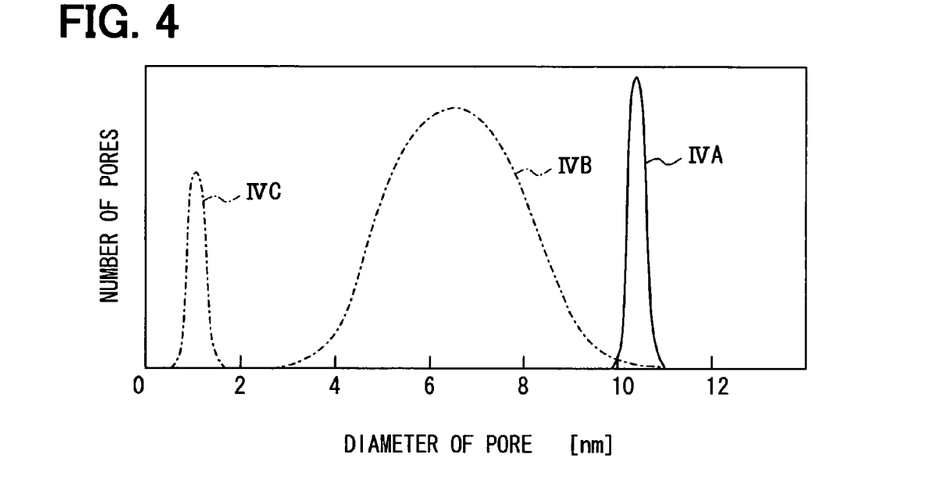
FIG. 4 is a graph showing a distribution of size of fine pores in inorganic material for providing a humidity sensitive film.
Figure 5A:
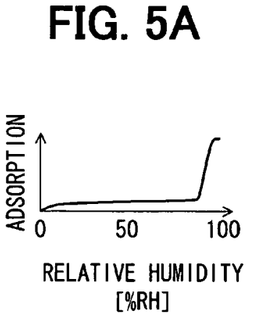
FIGS. 5A to 5C are graphs showing a relationship between relative humidity and adsorb amount of water molecules in different materials.
Figure 5B:
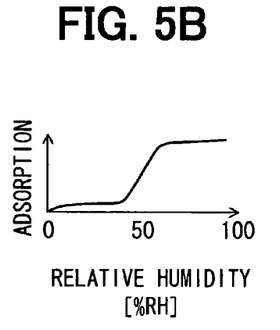
Figure 5C:
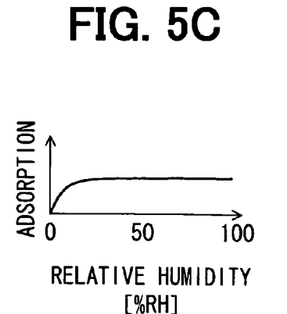

The relationship between the above predetermined relative humidity and the diameter of the fine pore will be explained with reference to FIGS. 4 and 5A to 5C. FIG. 4 shows distribution of the diameter of the fine pores for providing the humidity sensitive film 60. FIGS. 5A to 5C show a relationship between relative humidity and water adsorption when the humidity sensitive film 60 has a different diameter distribution of the fine pores. Here, a general Kelvin equation is well known for defining the capillary tube aggregation phenomenon.

In FIG. 4, a curve IVA shows that the diameter of the fine pores for providing the humidity sensitive film 60 is in a range between 10 nm and 11 nm, i.e., within a small range. In this case, the relationship between the water and the relative humidity is shown in FIG. 5A. When the relative humidity in the atmosphere is in a range between 0% and 5%, the moisture amount to be adsorbed in the humidity sensitive film 60 increases. When the relative humidity in the atmosphere is in a range between 5% and 95%, the moisture amount to be adsorbed in the humidity sensitive film 60 is substantially constant. When the relative humidity in the atmosphere is in a range between 95% and 100%, the moisture amount to be adsorbed in the humidity sensitive film 60 rapidly increases. Thus, when the diameter of the fine pores is in a range between 10 nm and 11 nm, the threshold of the capillary tube aggregation phenomenon is 95% in relative humidity. Specifically, the capillary tube aggregation phenomenon occurs when the relative humidity is about 95%.

In a case where the humidity sensitive film 60 has the above property, the detection sensitivity of the sensor 1 is extremely high when the sensor 1 detects the humidity in the atmosphere having the relative humidity higher than 95% since the capacitance change is very large with respect to the humidity change. Accordingly, the detection accuracy of the relative humidity is extremely high. However, the detection sensitivity of the sensor 1 is extremely low when the sensor 1 detects the humidity in the atmosphere having the relative humidity lower than 95% since the capacitance change is very small with respect to the humidity change. Accordingly, the detection accuracy of the relative humidity is extremely low, i.e., it is difficult to detect the relative humidity. Thus, when the humidity sensitive film 60 has the above property, the sensor 1 has such a detection property.

In FIG. 4, a curve IVB shows that the diameter of the fine pores for providing the humidity sensitive film 60 is in a range between 3 nm and 10 nm, i.e., within a wide range. In this case, the relationship between the water and the relative humidity is shown in FIG. 5B. When the relative humidity in the atmosphere is in a range between 0% and 5%, the moisture amount to be adsorbed in the humidity sensitive film 60 increases. When the relative humidity in the atmosphere is in a range between 5% and 45%, the moisture amount to be adsorbed in the humidity sensitive film 60 is substantially constant. When the relative humidity in the atmosphere is in a range between 45% and 55%, the moisture amount to be adsorbed in the humidity sensitive film 60 linearly increases. When the relative humidity in the atmosphere is in a range between 55% and 100%, the moisture amount to be adsorbed in the humidity sensitive film 60 is substantially constant. Thus, when the diameter of the fine pores is in a range between 3 nm and 10 nm, the threshold of the capillary tube aggregation phenomenon is 45% in relative humidity. Specifically, the capillary tube aggregation phenomenon occurs when the relative humidity is about 45%. When the relative humidity is about 55%, the water molecules penetrate in almost all of the fine pores so that the fine pores are saturate with moisture.

In a case where the humidity sensitive film 60 has the above property, the detection sensitivity of the sensor 1 is extremely low when the sensor 1 detects the humidity in the atmosphere having the relative humidity lower than 45% since the capacitance change is very small with respect to the humidity change. Accordingly, the detection accuracy of the relative humidity is extremely low, i.e., it is difficulty to detect the relative humidity. However, the detection sensitivity of the sensor 1 is extremely high when the sensor 1 detects the humidity in the atmosphere having the relative humidity in a range between 45% and 55% since the capacitance change is very large with respect to the humidity change. Accordingly, the detection accuracy of the relative humidity is extremely high. Further, the detection sensitivity of the sensor 1 is extremely low when the sensor 1 detects the humidity in the atmosphere having the relative humidity higher than 55% since the capacitance change is very small with respect to the humidity change. Accordingly, the detection accuracy of the relative humidity is extremely low, i.e., it is difficulty to detect the relative humidity. Thus, when the humidity sensitive film 60 has the above property, the sensor 1 has such a detection property.

In FIG. 4, a curve IVC shows that the diameter of the fine pores for providing the humidity sensitive film 60 is in a range between 1 nm and 2 nm, i.e., within a small range. In this case, the relationship between the water and the relative humidity is shown in FIG. 5C. When the relative humidity in the atmosphere is in a range between 0% and 10%, the moisture amount to be adsorbed in the humidity sensitive film 60 increases. When the relative humidity in the atmosphere is in a range between 10% and 100%, the moisture amount to be adsorbed in the humidity sensitive film 60 is substantially constant. Thus, when the diameter of the fine pores is in a range between 1 nm and 2 nm, the threshold of the capillary tube aggregation phenomenon is about 0% in relative humidity. Specifically, the capillary tube aggregation phenomenon occurs when the relative humidity is about 0%. When the relative humidity is about 10%, the water molecules penetrate in almost all of the fine pores so that the fine pores are saturate with moisture.

In a case where the humidity sensitive film 60 has the above property, the detection sensitivity of the sensor 1 is extremely high when the sensor 1 detects the humidity in the atmosphere having the relative humidity lower than 10% since the capacitance change is very large with respect to the humidity change. Accordingly, the detection accuracy of the relative humidity is extremely high. However, the detection sensitivity of the sensor 1 is extremely low when the sensor 1 detects the humidity in the atmosphere having the relative humidity higher than 10% since the capacitance change is very small with respect to the humidity change. Accordingly, the detection accuracy of the relative humidity is extremely low, i.e., it is difficult to detect the relative humidity. Thus, when the humidity sensitive film 60 has the above property, the sensor 1 has such a detection property.

Here, a conventional humidity sensor having a humidity sensitive film made of organic polymer can detect relative humidity in a range between 5% and 90% with a substantially constant detection accuracy. However, when the conventional humidity sensor detects the humidity in atmosphere having relative humidity higher than 95%, it is difficult to detect the relative humidity with high detection accuracy since capacitance change rate with respect to humidity change is changed.

In this embodiment, the diameter of the fine pore of the inorganic material for providing the humidity sensitive film 60 is set to be in a range between 10 nm and 11 nm so that the sensor 1 has the property shown in FIG. 5A. Thus, the sensor 1 can detect the relative humidity with high detection accuracy even when the relative humidity is comparatively high.

The processing circuit will be explained as follows with reference to FIGS. 6 to 8.

Figure 6:
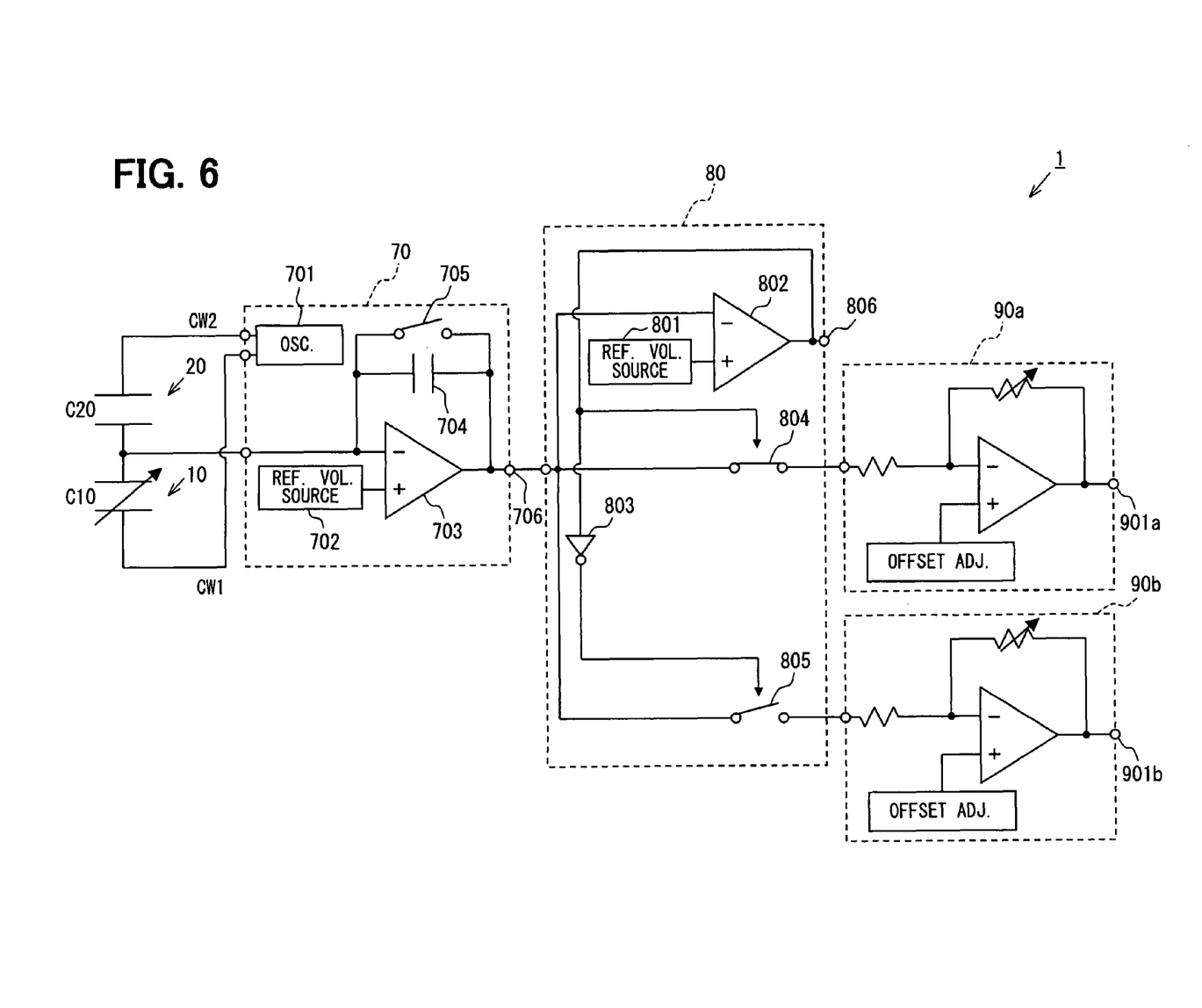
FIG. 6 is a circuit diagram showing an equivalent circuit of the humidity sensor.

As shown in FIG. 6, the processing circuit of the sensor 1 includes a switched capacitor (i.e., SC) circuit, a switching circuit 80, a first amplifier circuit 90*a*, a second amplifier circuit 90*b* and the like. The SC circuit 70 converts the capacitance difference between a variable capacitor C10 having a variable capacitance and a fixed capacitor C20 having a fixed capacitance to a voltage. The variable capacitor C10 corresponds to the first sensor element 10, and the variable capacitance is variable in accordance with the relative humidity in the atmosphere. The fixed capacitor C20 corresponds to the second sensor element 20, and the fixed capacitance is not variable in accordance with the relative humidity. The switching circuit 80 switches the amplification factor. The first amplifier circuit 90*a* has an amplification factor of, for example, sixty-fold, and the second amplifier circuit 90*b* has an amplification factor of, for example, twelve-fold.

Specifically, in FIG. 6, the SC circuit 70 includes an oscillation circuit 701, a reference voltage source 702, a differential amplifier circuit 703, a capacitor 704, an analog switch 705, a sample holding circuit (not shown) and the like. A first carrier wave CW1 is a rectangular wave, and a second carrier wave CW2 is also a rectangular wave. Each of the first and second carrier waves CW1, CW2 has the same amplitude of, for example, five volts. The phase difference between the first and second carrier waves CW1, CW2 is 180 degrees. The oscillation circuit 701 applies the first and second carrier waves CW1, CW2 to the variable capacitor C10 and the fixed capacitor C20, respectively. The reference voltage source 702 outputs a bias voltage of, for example, 2.5 volts. The differential amplifier circuit 703 differentially amplifies the bias voltage and a middle voltage between the variable capacitor C10 and the fixed capacitor C20. The capacitor 704 has a predetermined capacitance.

Figure 7:
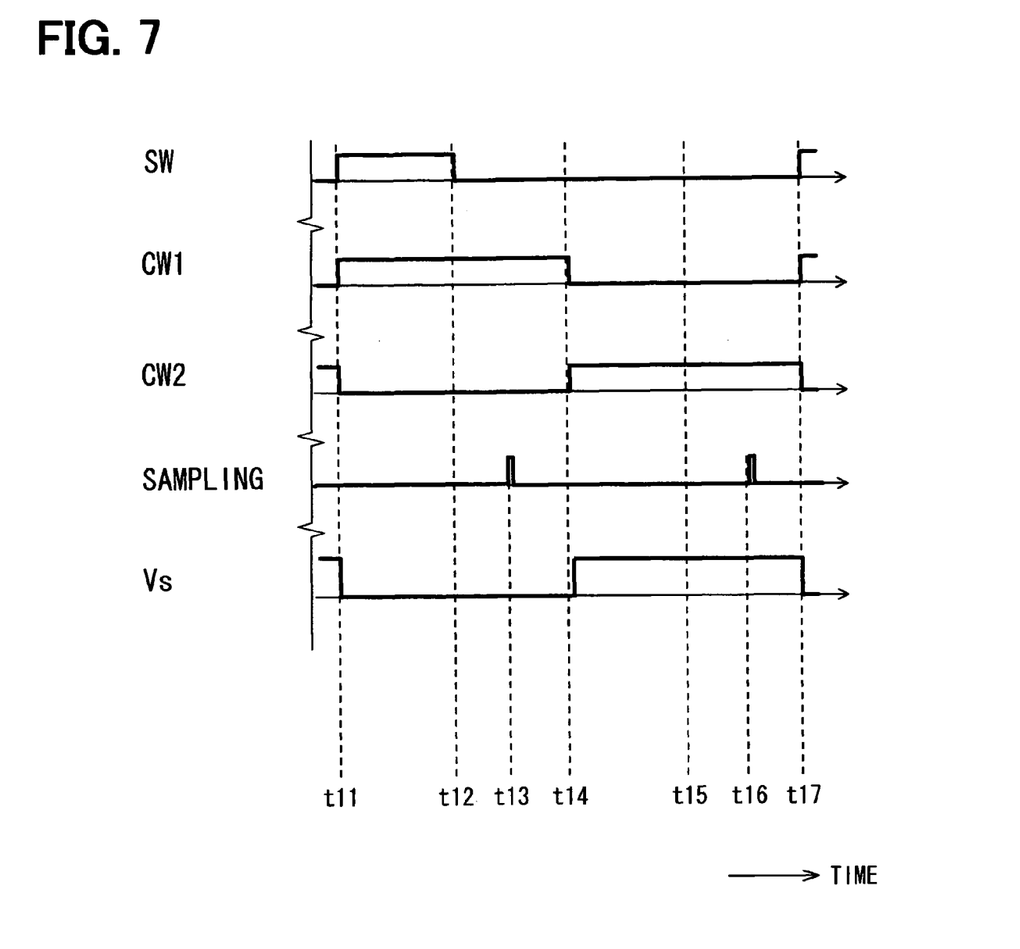
FIG. 7 is a timing chart showing C-V converting operation of a switched capacitor.
Figure 8A:
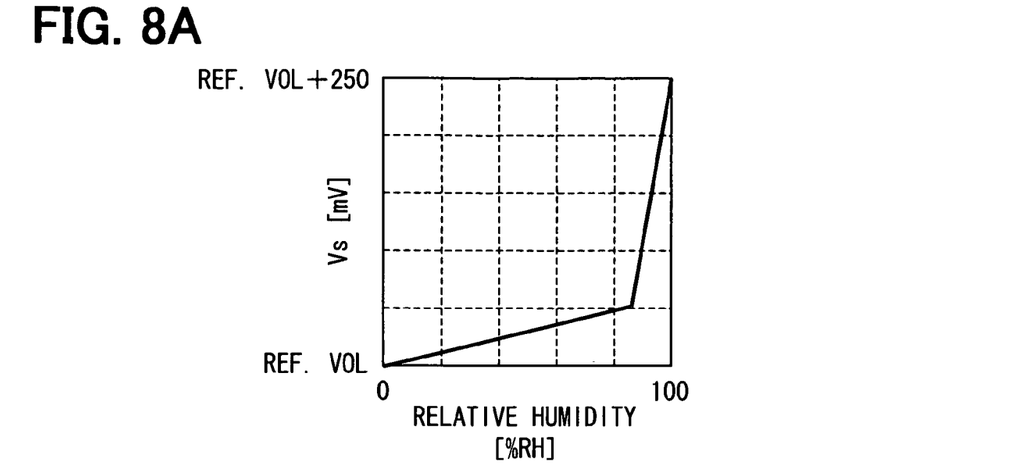
FIGS. 8A to 8C are graphs showing a relationship between relative humidity and output voltage in different points.
Figure 8B:
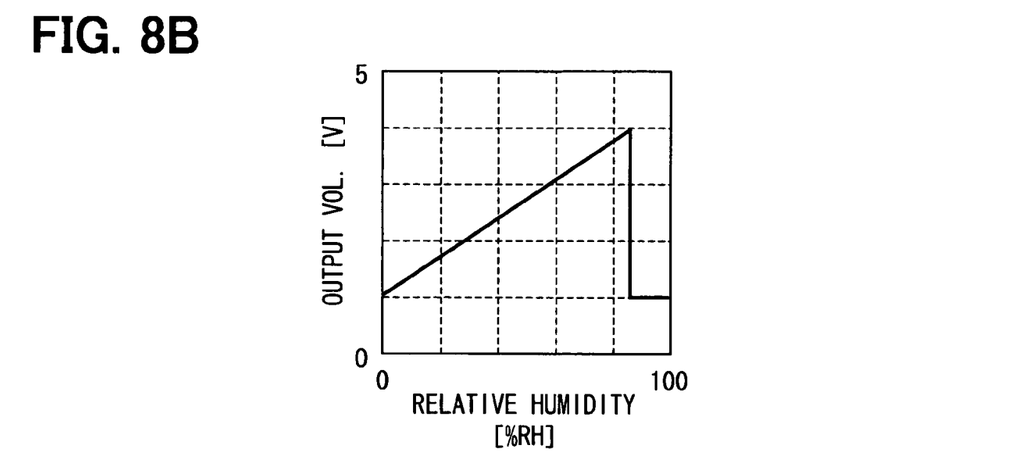
Figure 8C:
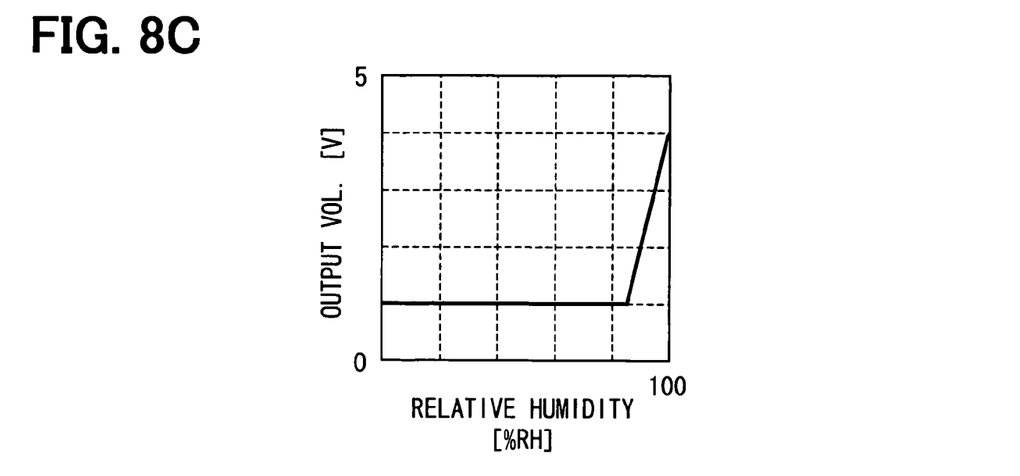

The SC circuit 70 performs C-V conversion, which is shown, for example, in FIG. 7. The C-V conversion has a cycle of reset, sample holding, carrier wave switching, and sample holding. This cycle is performed every 10 microseconds.

At the time t11, the analog switch 705 turns on, so that the capacitor 704 discharges, i.e., the capacitor 704 is reset. At the same time of discharge of the capacitor 704, the first carrier wave CW1 rises (i.e., turns to a high level), and the second carrier wave CW2 decays (i.e., turns to a low level). When the capacitance of the variable capacitor C10 is larger than the capacitance of the fixed capacitor C20, the variable capacitor C10 is charged in accordance with a voltage applied to the electrode 10*a* of the variable capacitor C10 on the oscillation circuit side, and the fixed capacitor C20 is charged in accordance with a voltage applied to the electrode 20*b* of the fixed capacitor C20 on the oscillation circuit side. Here, the electrode 10*b* of the variable capacitor C10 on the differential amplifier circuit side has a state in which negative charges are dominant, and the electrode 20*a* of the fixed capacitor C20 on the differential amplifier circuit side has a state in which negative charges are dominant.

Next, at the time t12, the analog switch 705 turns off, so that the electrode 10*b* of the variable capacitor C10, the electrode 20*a* of the fixed capacitor C20 and an electrode of the capacitor 704 on a reverse input terminal side of the differential amplifier circuit 703 provide a closed circuit. Thus, the charge in the variable capacitor C10 and the fixed capacitor C20, which are charged during the time between t11 and t12, is preserved. Under this condition, at the time t13, the output voltage Vs of the SC circuit 70 is sampled so that the output voltage Vs is temporarily stored in a certain memorizing means.

At the time t14, the first carrier wave CW1 decays, i.e., turns to a low level, and the second carrier wave CW2 rises, i.e., turns to a high level. When the carrier waves CW1, CW2 are reversed, the electrode 10*b* of the variable capacitor C10 has a state in which positive charges are dominant, and the electrode 20*a* of the fixed capacitor C20 has a state in which positive charges are dominant. However, since the electrode 10*b* of the variable capacitor C10, the electrode 20*a* of the fixed capacitor C20 and an electrode of the capacitor 704 on a reverse input terminal side of the differential amplifier circuit 703 provide the closed circuit, the charge in the closed circuit is preserved. Thus, the negative charges in the electrode 10*b* of the variable capacitor C10 and the electrode 20*a* of the fixed capacitor C20, which overflows from equilibrium state of charges, moves to the electrode of the capacitor 704 on the reverse input terminal side of the differential amplifier circuit 703. This charge transfer provides to charge the positive charges in the electrode of the capacitor 704 on the output terminal side of the differential amplifier circuit 703. Accordingly, in view of a relationship of "the amount of accumulated charges is equal to a capacitance multiplied by a potential difference (i.e., Charge=Capacitance×Potential Difference)," the output voltage Vs of the SC circuit 70 changes by a voltage in proportion to the transferred charges and in reverse proportion to the capacitance of the capacitor 704.

Thus, the changed output voltage Vs is output from the output terminal 607 of the SC circuit 70. At the time t16, the output voltage Vs of the SC circuit 70 is sampled after the charge transfer is completed and stabilized. The output voltage Vs is temporarily stored in the certain memorizing means. At the time t17, the cycle of the above process returns so that the cycle starts to repeat.

The relative humidity is detected based on the voltage sampled at the time t13 is differentially calculated from the voltage sampled at the time t16. Further, in this embodiment, the humidity sensitive film 60 has the property shown in FIG. 5A, thereby, the relationship between the relative humidity in the atmosphere and the output voltage Vs from the output terminal 706 is shown, for example, in FIG. 8A. When the relative humidity is in a range between 0% and 95%, the output voltage Vs increases linearly from 0 mV to 50 mV. When the relative humidity is in a range between 95% and 100%, the output voltage Vs increases linearly from 50 mV to 250 mV.

As shown in FIG. 6, the switching circuit 80 includes a comparator 802, an inverter 803, a first analog switch 804, a second analog switch 805, an output terminal 806 and the like. The comparator 802 compares the bias voltage of "50 mV" output from the reference voltage source 801 with the output voltage Vs from the output terminal 706. Further, the comparator 802 outputs an output voltage based on the compared result, the output voltage being a voltage corresponding to the high logic level Hi or a voltage corresponding to the low logic level Lo. The inverter 803 reverses the output voltage from the comparator 802. The first analog switch 804 switches on when the voltage corresponding to the high logic level Hi is applied to the switch 804 from the comparator 802. The second analog switch 805 switches on when the voltage corresponding to the high logic level Hi is applied to the switch 805 from the inverter 803. Here, the bias voltage of the reference voltage source 801 is set to be 50 mV, which corresponds to an inflection point of the characteristics of the output voltage Vs. Specifically, at the inflection point, the slope of the linear curve changes.

The switching circuit 80 switches between the first and second amplifier circuits 90a, 90b, i.e., the switching circuit 80 performs a switching operation of the amplification factor.

When the relative humidity is in a range between 0% and 95%, the output voltage Vs in a range between 0 mV and 50 mV is output from the output terminal 706, and then, the output voltage Vs is input in the switching circuit 80. Next, the output voltage of the SC circuit 70 and the bias voltage are compared in the comparator 802. In this case, the bias voltage is larger than the output voltage, thereby, the voltage corresponding to the high logic level Hi is output from the comparator 802. Thus, when the voltage corresponding to the high logic level Hi is output, the analog switch 804 turns on, and the second analog switch 805 turns off. The output voltage Vs of the output terminal 706 is amplified sixty-fold by the first amplifier circuit 90a. Accordingly, the output voltage of the output terminal 901a in the first amplifier circuit 90a is changed in a range between 1.0 V and 4.0 V with respect to the relative humidity in a range between 0% and 95%, as shown in FIG. 8B. Here, when the relative humidity is in a range between 95% and 100%, the output voltage of the output terminal 901a is constant to be 1.0 V, since off-set adjustment is performed in the first amplifier circuit 90a.

When the relative humidity is in a range between 95% and 100%, the output voltage Vs in a range between 50 mV and 250 mV is output from the output terminal 706. Then, the output voltage Vs is input in the switching circuit 80. Next, the output voltage of the SC circuit 70 and the bias voltage are compared in the comparator 802. In this case, the bias voltage is smaller than the output voltage Vs, thereby, the voltage corresponding to the low logic level Lo is output from the comparator 802. Thus, when the voltage corresponding to the low logic level Lo is output, the analog switch 804 turns off, and the analog switch 805 turns on. The output voltage Vs of the output terminal 706 is amplified twelve-fold by the second amplifier circuit 90b. Accordingly, the output voltage of the output terminal 901b in the second amplifier circuit 90b is changed in a range between 1.0 V and 4.0 V with respect to the relative humidity in a range between 95% and 100%, as shown in FIG. 8C. Here, when the relative humidity is in a range between 0% and 95%, the output voltage of the output terminal 901b is constant to be 1.0 V, since off-set adjustment is performed in the second amplifier circuit 90b.

On the bases of the output voltage of the output terminal 806 in the switching circuit 80, the output voltage of the output terminal 901a in the first amplifier circuit 90a, and the output voltage of the output terminal 901b in the second amplifier circuit 90b, the relative humidity is detected, so that the relative humidity can be detected in a wide range with high accuracy.

The humidity sensor 1 is suitably used for an air conditioning system so that a window in a vehicle is protected from being fogged. Specifically, the humidity sensor 1 can detect the relative humidity with high accuracy even when the relative humidity is comparatively high. Accordingly, just before dew condensation occurs on the window, i.e., just before the relative humidity is near 100%, the air conditioning system starts to operate so that the relative humidity is reduced. Thus, the dew condensation is prevented from occurring. Thus, the humidity sensor 1 may be used as a dew condensation sensor.

Figure 9:
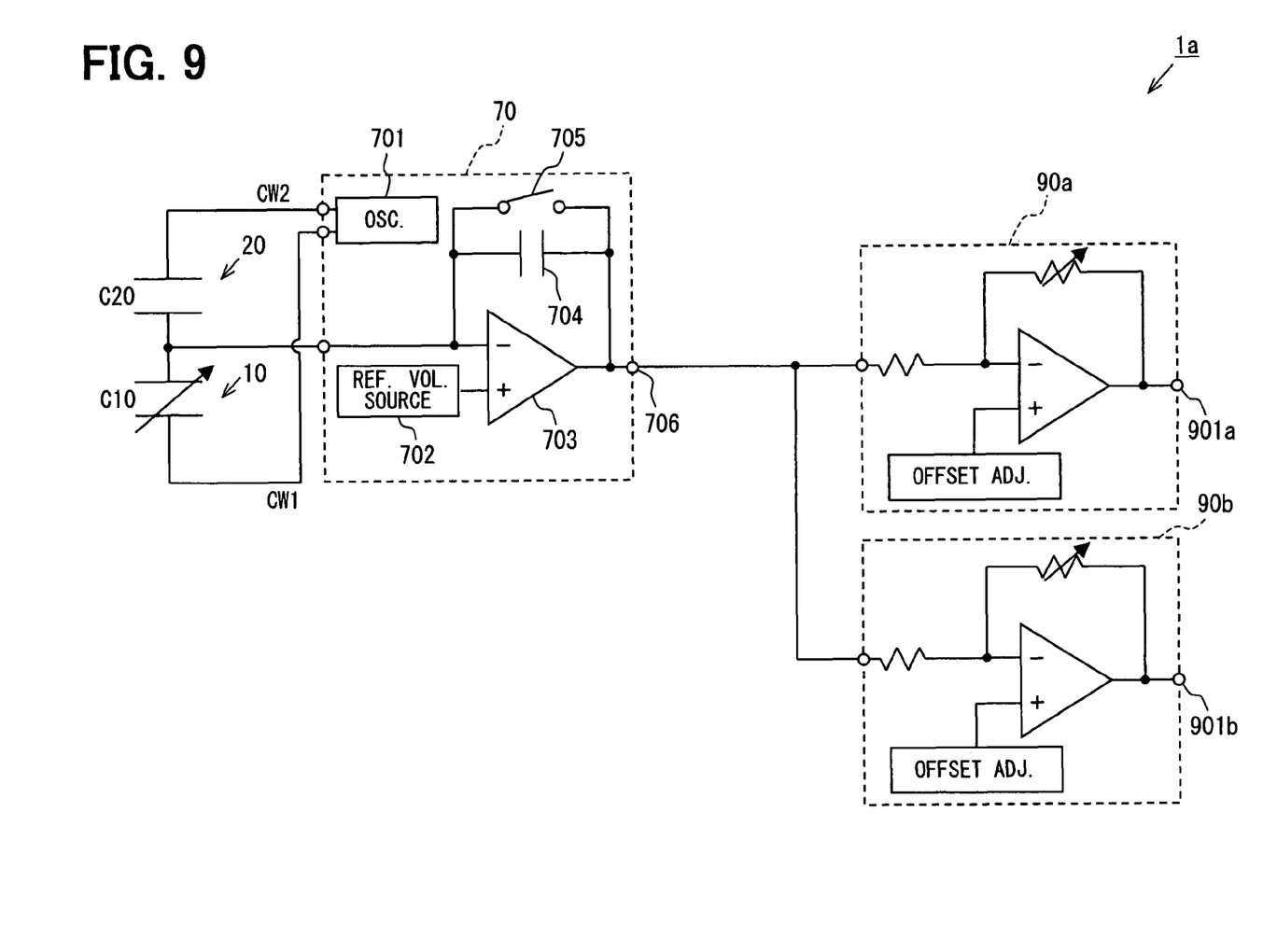
FIG. 9 is a circuit diagram showing an equivalent circuit of a humidity sensor according to a first modification of the first embodiment.

The first amplifier circuit 90a having the predetermined amplification factor for detecting the relative humidity lower than 95% and the second amplifier circuit 90b having the predetermined amplification factor for detecting the relative humidity higher than 95% are switched. Thus, the sensor 1 has two amplifier circuits so that the amplification factor is switched. Alternatively, as shown in FIG. 9, a humidity sensor 1a may have no switching circuit 80. The sensor 1a has two amplifier circuits 90a, 90b. Based on the output voltage of the output terminal 901a in the first amplifier circuit 90a, the relative humidity in a range between 5% and 95% is detected. Based on the output voltage of the output terminal 901b in the second amplifier circuit 90b, the relative humidity in a range between 95% and 100% is detected.

Figure 10:
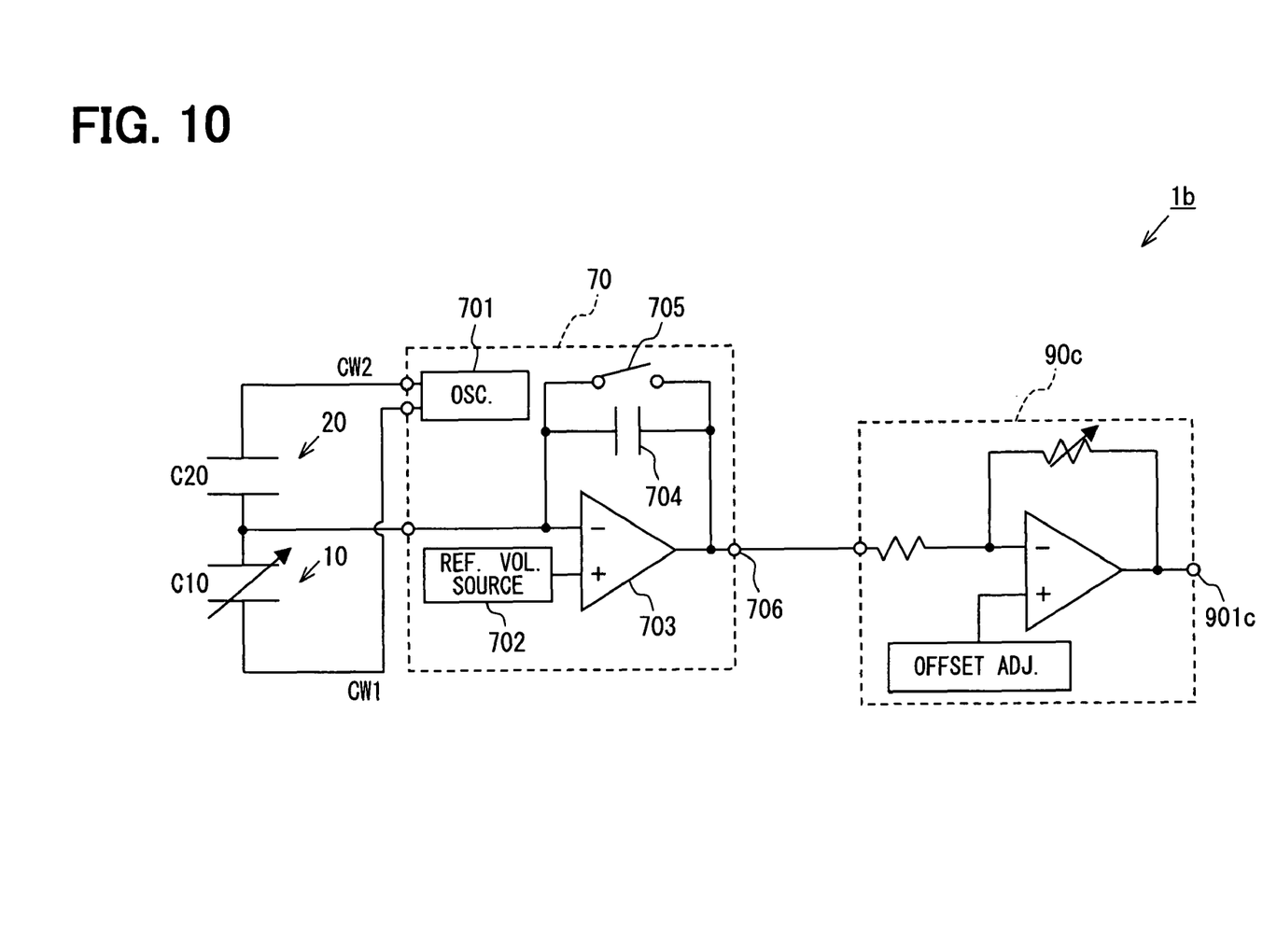
FIG. 10 is a circuit diagram showing an equivalent circuit of a humidity sensor according to a second modification of the first embodiment.

Alternatively, as shown in FIG. 10, another humidity sensor 1b may have no switching circuit 80, and have a third amplifier circuit 90c instead of the first and second amplifier circuits 90a, 90b. The third amplifier circuit 90c is capable of setting an amplification factor variably. Thus, the number of amplifier circuits is reduced, so that the dimensions of the sensor 1b are reduced. Further, the sensor 1b may have no amplifier circuit 90c, so that the dimensions of the sensor 1c are much reduced.

Figure 11:
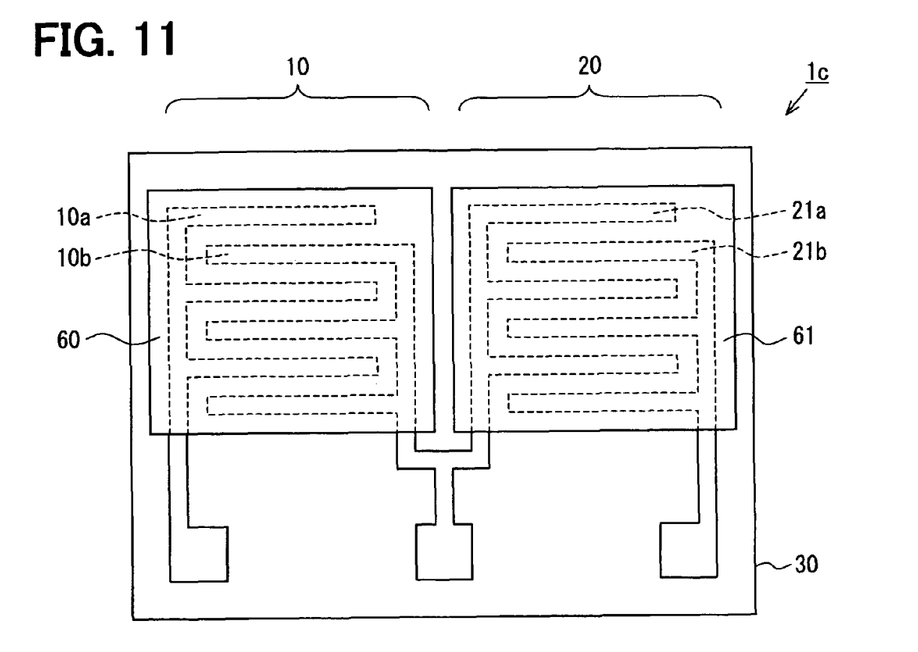
FIG. 11 is a plan view showing a humidity sensor according to a third modification of the first embodiment.

The sensor 1 includes the second sensor element 20 that has the electrodes 20a, 20b and has the capacitance, which is not changed in accordance with the relative humidity. Alternatively, as shown in FIG. 11, a humidity sensor 1c includes a third sensor element 21 and the first sensor element 10. The third sensor element 21 as a third capacitive element includes a pair of comb-teeth electrodes 21a, 21b and a humidity sensitive film 61 made of organic polymer. The third sensor element 21 corresponds to a conventional humidity sensor element. The capacitance of the third sensor element 21 changes linearly in accordance with the relative humidity. Accordingly, when the relative humidity is in a range between 5% and 90%, the third sensor element 21 can detect the relative humidity with constant detection accuracy. The first sensor element 10 can detect the relative humidity with high accuracy when the relative humidity is higher than 95% since the change ratio of the capacitance is much large with respect to the humidity change. However, when the relative humidity is smaller than 95%, the change ratio of the capacitance in the first sensor element 10 is almost zero with respect to the humidity change, thereby, the detection accuracy of the relative humidity is low. Since the sensor 1c has both of the first and third sensor elements 10, 21, the sensor 1c can detect the relative humidity with conventional detection accuracy when the relative humidity is in a range between 5% and 95%, and the sensor 1c can detect the relative humidity with detection accuracy higher than the conventional detection accuracy when the relative humidity is in a range between 95% and 100%.

Figure 12:
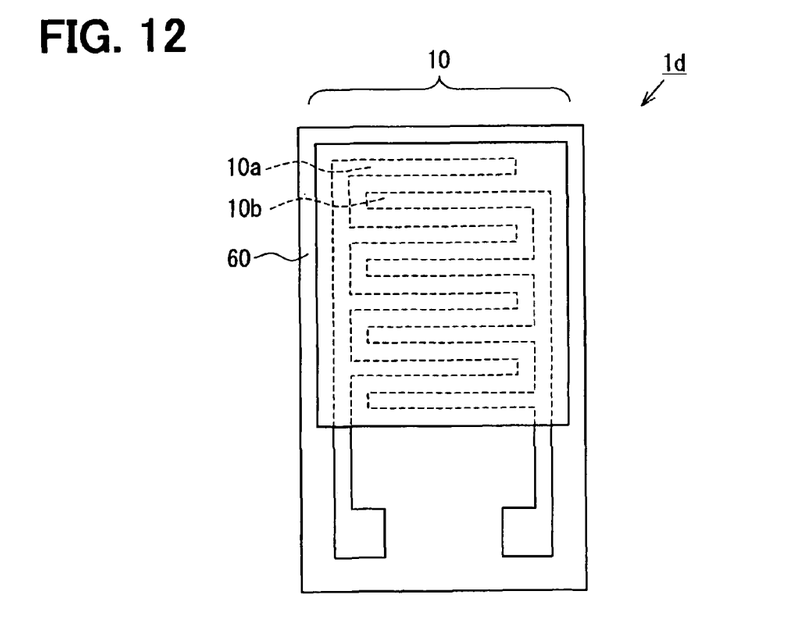
FIG. 12 is a plan view showing a humidity sensor according to a fourth modification of the first embodiment.

Although the sensor 1, 1a-1c includes two humidity sensor elements 10, 20, 21, the sensor may have one humidity sensor element 10, as shown in FIG. 12. Although the sensor 1, 1a-1c includes the C-V converter circuit, i.e., the SC circuit 70 for converting the capacitance difference to the voltage, the sensor 1d may include a general resonant circuit. Specifically, a R-C oscillation circuit is formed by the first sensor element 10 and a resistor having a predetermined resistance. When the relative humidity is changed, the capacitance of the first sensor element 10 is changed. Based on a resonant frequency change in accordance with the capacitance change, the relative humidity is detected.

Although the sensor 1, 1a-1d includes a pair of comb-teeth electrode 10a, 10b, 20a, 20b, 21a, 21b, the electrode in the sensor 1, 1a-1d may have another electrode shape. For example, the sensor 1, 1a, 1d may have a pair of plate electrodes, which sandwiches a humidity sensitive film.

Although the inorganic material providing the humidity sensitive film 60 has fine pores in a range between 10 nm and 11 nm so that the sensor 1, 1a-1d has the sensor characteristics shown in FIG. 5A, the fine pores may be in a range between 10 nm and 50 nm so that the sensor 1, 1a-1d has sensor characteristics similar to that in FIG. 5A.

The fine pores may be in a range between 3 nm and 10 nm so that the sensor has the sensor characteristics shown in FIG. 5B. Alternatively, the fine pores may be in a range between 1 nm and 2 nm so that the sensor has the sensor characteristics shown in FIG. 5C. In both cases, the range of the diameter of the fine pores may be set appropriately in accordance with required relative humidity range, in which the relative humidity is detected with high accuracy.

Second Embodiment

Figure 13:
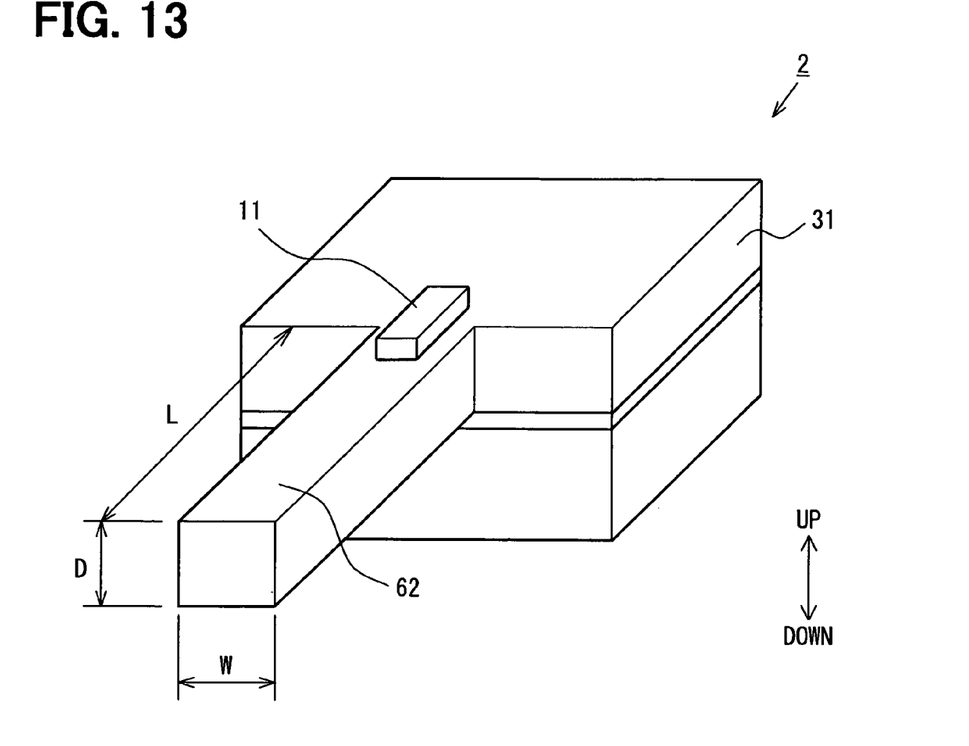
FIG. 13 is a perspective view showing a humidity sensor according to a second embodiment.

FIG. 13 shows a humidity sensor 2 according to a second embodiment. The humidity sensor 2 includes a cantilever 62 as a humidity sensitive member, a support member 31, a strain gauge 11 and a processing circuit (not shown). The support member 31 supports the cantilever 62 at one portion in such a manner that the cantilever 62 is capable of vibrating. The cantilever 62 is made of humidity sensitive material, and is capable of vibrating with a resonant frequency in accordance with weight of moisture adsorbed in the humidity sensitive material. The strain gauge 11 as a detector outputs an electric signal to the processing circuit, the electric signal corresponding to amplitude of the cantilever 62. The processing circuit processes the electric signal from the strain gauge 11.

The cantilever 62 has a rectangular shape and protrudes from a sidewall of the support member 31. The cantilever 62 is capable of vibrating in an up-down direction around a support portion of the support member 31 as a vibrating point. The humidity sensitive material of the cantilever 62 is organic material having multiple fine pores for adsorbing moisture. The longitudinal length of the cantilever 62 is defined as D, the longitudinal length as L, and the width as W. The density of the cantilever 62 is defined as $\rho$, the Young's modulus is defined as E, the cross sectional secondary moment is defined as I, and the gravity acceleration is defined as g. The resonant frequency of the primary vibration of the cantilever 62 is defined as follows.

$$\text{(Resonant Frequency)} = \frac{\lambda^3}{2\pi L^2} \sqrt{\frac{E \times I \times g}{\rho \times D \times W}} \quad \text{(F1)}$$

Here, when the relative humidity in the atmosphere is high, the cantilever 62 adsorbs much amount of moisture. Thus, the density $\rho$ becomes large. In this case, the denominator in the above formula F1 becomes large, thereby, the resonant frequency becomes small. When the relative humidity in the atmosphere is low, the cantilever 62 does not adsorb moisture substantially. Thus, the density $\rho$ becomes small. In this case, the denominator in the above formula F1 becomes small, thereby, the resonant frequency becomes large. Thus, the resonant frequency of the cantilever 62 is changed in accordance with the relative humidity. Accordingly, based on the resonant frequency change, the relative humidity is detected.

The strain gauge 11 is disposed on a part of the surface of the support member 31, the part corresponding to the support portion of the cantilever 62. The strain gauge 11 is bonded to the support member 31. The strain gauge 11 outputs the electric signal corresponding to the amplitude of vibration of the cantilever 62 to the processing circuit.

The output signal from the strain gauge 11 is introduced into the processing circuit, and then, the output signal is processed appropriately, so that the resonant frequency is calculated. Based on the calculated resonant frequency, the relative humidity is detected.

Although the sensor 2 includes the strain gauge 11, the sensor 2 may include another element such as a Piezo electric element for converting the vibration of the cantilever 62 to the electric signal.

The cantilever 62 is supported on the support member 31 at one portion. Alternatively, the cantilever 62 may be supported on the support member 31 at multiple portions. As long as the cantilever 62 is capable of vibrating with the resonant frequency corresponding to the weight of moisture adsorbed in the humidity sensitive material, the cantilever may be supported on the support member 31 in any support manner.

MODIFICATIONS

In the first embodiment, the sensor 1 is a capacitive humidity sensor, and, in the second embodiment, the sensor 2 is a vibration type humidity sensor. Alternatively, the sensor 1, 2 may detect relative humidity in any manner as long as the sensor detects the humidity change based on change of physical quantity of the humidity sensitive material in the sensor, and the humidity sensitive material is inorganic material having multiple fine pores for adsorbing moisture.

While the invention has been described with reference to preferred embodiments thereof, it is to be understood that the invention is not limited to the preferred embodiments and constructions. The invention is intended to cover various modification and equivalent arrangements. In addition, while the various combinations and configurations, which are preferred, other combinations and configurations, including more, less or only a single element, are also within the spirit and scope of the invention.

What is claimed is:

1. A humidity sensor for detecting humidity in atmosphere comprising:
    a humidity sensing element including a humidity sensitive film and a pair of first electrodes;
    a processing circuit, wherein:
    the humidity sensitive film has a dielectric constant, which is variable in accordance with moisture adsorbed in the humidity sensitive film;
    the pair of first electrodes detects capacitance of the humidity sensitive film and outputs a signal corresponding to the capacitance;
    the processing circuit processes the signal from the pair of first electrodes;
    the humidity sensor is a capacitive humidity sensor for detecting relative humidity based on the dielectric constant of the humidity sensitive film;
    the humidity sensitive film is made of inorganic material having a plurality of fine pores for adsorbing the moisture in the atmosphere;
    a diameter of each of the fine pores is disposed within a range around a predetermined center value so that capillary tube aggregation phenomenon occurs at a predetermined relative humidity;
    the capillary tube aggregation phenomenon is defined in such a manner that a plurality of water molecules in the atmosphere rapidly penetrate into the fine pores at the predetermined relative humidity;
    the capacitance of the humidity sensitive film has a change rate with respect to the relative humidity; and
    the change rate of the capacitance when the relative humidity in the atmosphere is higher than the predetermined relative humidity is larger than the change rate of the capacitance when the relative humidity in the atmosphere is lower than the predetermined relative humidity; and
    a capacitive element having a pair of second electrodes, wherein
    the capacitive element has a capacitance, which is substantially constant with respect to the relative humidity;
    the processing circuit includes a C-V converter circuit for converting a capacitance difference between the pair of second electrodes and the pair of first electrodes to a voltage; and
    the humidity sensor detects the relative humidity based on the voltage output from the C-V converter circuit,
    wherein:
    the processing circuit further includes a first amplifier and a second amplifier;
    the first amplifier amplifies the voltage output from the C-V converter circuit with a first amplification factor so that the relative humidity higher than the predetermined relative humidity is detected; and
    the second amplifier amplifies the voltage output from the C-V converter circuit with a second amplification factor so that the relative humidity lower than the predetermined relative humidity is detected.

2. The sensor according to claim 1, wherein:
the change rate of the capacitance becomes large as a full width at half maximum (FWHM) of a predetermined distribution over the range becomes narrower.

3. The sensor according to claim 2, wherein:
the range is between 10 nanometers and 50 nanometers.

4. The sensor according to claim 3, wherein:
the range is between the predetermined center value minus 1 nanometer and the predetermined center value plus 1 nanometer.

5. The sensor according to claim 2, wherein:
the predetermined center value is 10.5 nanometers; and
the range is between 10 nanometers and 11 nanometers.

6. The sensor according to claim 1, wherein:
the pair of first electrodes is covered with the humidity sensitive film; and
each first electrode has a comb-teeth shape.

7. The sensor according to claim 1, wherein:
the pair of first electrodes sandwiches the humidity sensitive film; and
each first electrode has a plate shape.

8. The sensor according to claim 1, wherein:
the processing circuit further includes an amplifier for amplifying the voltage from the C-V converter circuit with a predetermined amplification factor.

9. The sensor according to claim 1, wherein:
the processing circuit further includes a switching circuit for switching between the first and second amplifiers based on the voltage output from the C-V converter circuit.

* * * * *